United States Patent [19]
Schmidt

[11] Patent Number: 5,928,130
[45] Date of Patent: Jul. 27, 1999

[54] APPARATUS AND METHOD FOR IMPLANTING RADIOACTIVE SEEDS IN TISSUE

[76] Inventor: Bruno Schmidt, c/o Integ, 2800 Patton Rd., Roseville, Minn. 55113

[21] Appl. No.: 09/039,434

[22] Filed: Mar. 16, 1998

[51] Int. Cl.⁶ .................................................. A61M 36/12
[52] U.S. Cl. ................................................................ 600/7
[58] Field of Search ............................. 600/1–8; 604/60, 604/62, 64

[56] References Cited

U.S. PATENT DOCUMENTS

| | | | |
|---|---|---|---|
| 3,744,493 | 7/1973 | Booher et al. | 604/62 |
| 4,086,914 | 5/1978 | Moore | 600/7 |
| 5,242,373 | 9/1993 | Scott et al. | 600/7 |

*Primary Examiner*—Cary O'Connor
*Assistant Examiner*—Eric F. Winakur
*Attorney, Agent, or Firm*—Stanley M. Miller, P.A.

[57] ABSTRACT

A tool for implanting radioactive seeds for therapeutic purposes into living tissue such as a prostate gland includes an elongate hollow needle, an elongate hollow sleeve, and an elongate push rod. A plurality of axially aligned seeds and spacers are loaded into the sleeve, the sleeve is slideably inserted into the hollow needle, the needle is introduced into the tissue at a preselected site, and the push rod is used in a procedure that implants one or more seeds and spacers into the tissue. The sleeve is transparent or translucent so that the number of seeds and spacers remaining within the sleeve at any time is visually ascertainable.

10 Claims, 3 Drawing Sheets

APPARATUS AND METHOD FOR IMPLANTING RADIOACTIVE SEEDS IN TISSUE

BACKGROUND OF THE INVENTION

1. Field of the Invention

This invention relates, generally, to devices and methods used when implanting tumor-fighting radioactive seeds in living tissue such as a prostate gland for therapeutic purposes. More particularly, it relates to a brachytherapy device having a simple structure and which houses a plurality of seeds in the absence of a seed magazine.

2. Description of the Prior Art

A co-pending disclosure by the present inventor, filed Dec. 12, 1997 bearing Ser. No. 08/989,727, and entitled "Interstitial Brachytherapy Device And Method" is believed to be the prior art most pertinent to this disclosure.

In the earlier invention, a plurality of vertically stacked radioactive seeds are loaded into a magazine. A highly novel bias means is used to urge the seeds, sequentially, into a discharge chamber of the magazine. A hollow needle and a plunger rod are then used to deposit one or more seeds into the prostate gland.

A drawback of the just-mentioned inventive device is that the magazine and the bias means are made of plastic and have some bulk; although plastic is inexpensive, a device made with less plastic would be less expensive. Moreover, the earlier device, although of simple construction, nonetheless has some mechanical complexity. What is needed, then, is a seed-implanting device that uses less materials, which is very simple in structure, yet which performs the same function as said earlier invention.

However, in view of the art considered as a whole at the time the present invention was made, it was not obvious to those of ordinary skill in this art how these needs could be met.

SUMMARY OF THE INVENTION

The long-standing but heretofore unfulfilled need for an apparatus that overcomes the limitations of the prior art is now met by a new, useful, and nonobvious invention. The present invention provides a tool for implanting radioactive seeds in a prostate gland or other living tissue. The tool includes an elongate hollow needle having a pointed leading end for facilitating introduction of said needle into tissue at a preselected site, an elongate hollow sleeve having an external diameter slightly less than an internal diameter of the hollow needle, a plurality of radioactive seeds and nonradioactive spacers slideably received within a hollow interior of the elongate sleeve, said seeds and spacers having a common external diameter slightly less than an internal diameter of said sleeve, and an elongate push rod having a longitudinal extent substantially equal to a longitudinal extent of the elongate sleeve. Seeds and spacers are preloaded into the elongate sleeve, and the hollow needle slideably receives the loaded sleeve. The push rod holds the seeds and spacers in place as the hollow needle and sleeve are retracted to leave the seeds and spacers in the tissue being treated.

The elongate sleeve has a longitudinal extent substantially equal to a longitudinal extent of the hollow needle, and the push rod also has a longitudinal extent substantially equal to a longitudinal extent of the hollow needle.

It is a primary object of this invention to provide a seed-implantation tool of simple yet elegant design.

A closely related object is to provide a seed-implantation tool that is inexpensive to manufacture.

Another object is to provide a tool that is easy to use.

Still another object is to provide a tool that enables a physician to determined quickly and easily the number of seeds and spacers that have been implanted during a procedure.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
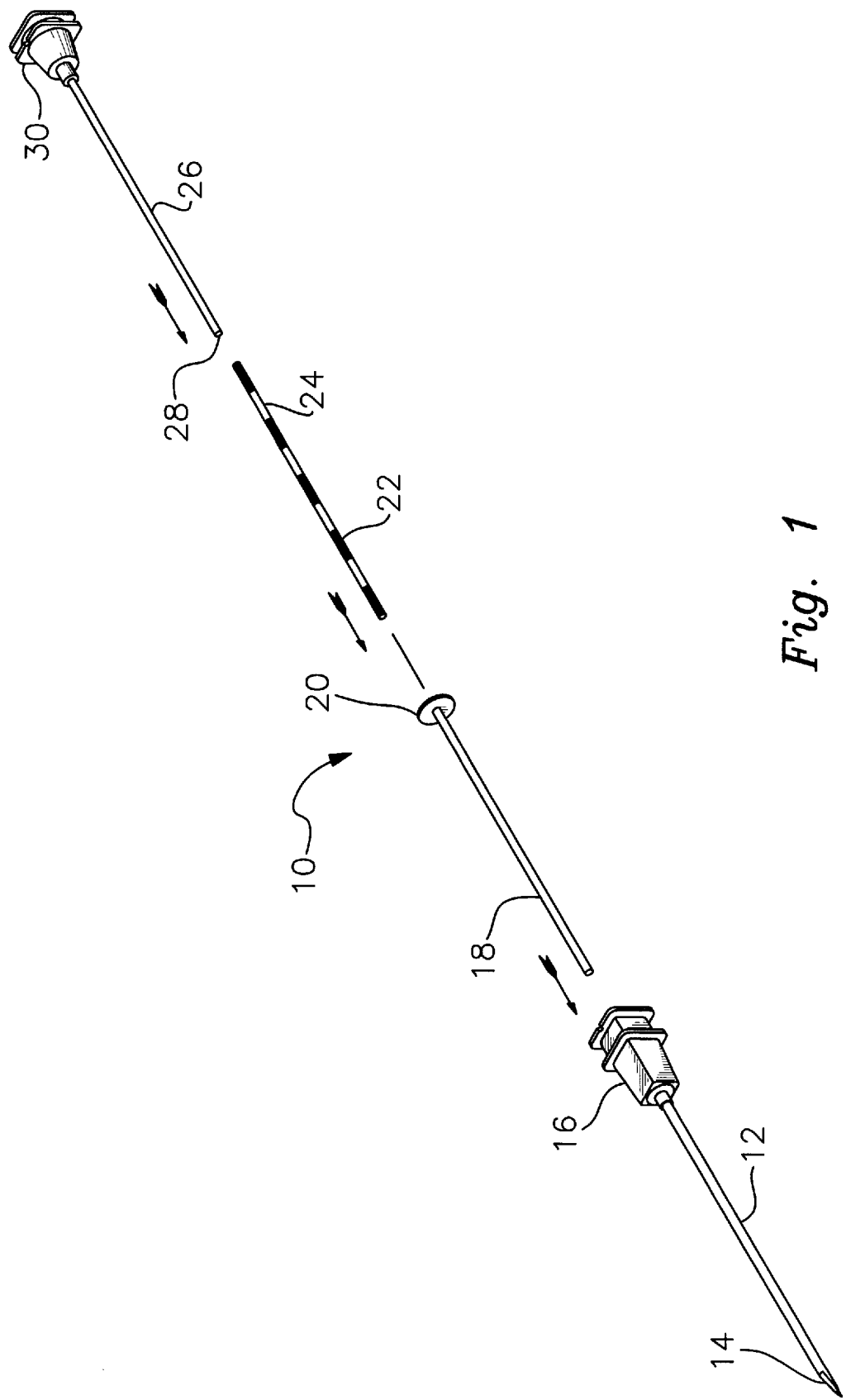
FIG. 1 is an exploded perspective view of the novel apparatus.

Referring now to FIG. 1, it will there be seen that an exemplary embodiment of the invention is denoted as a whole by the reference numeral 10.

Novel seed implanter 10 includes elongate hollow needle 12 having a pointed leading end 14 and a hollow hub 16 of truncate longitudinal extent at its trailing end. Pointed leading end 14 facilitates introduction of needle 12 into living tissue in the well-known way, and hollow hub 16 provides a handle means to facilitate handling of hollow needle 12.

Novel tool 10 further includes hollow elongate sleeve 18 having a flat, disc-shaped head 20 integrally formed with or mounted to its trailing end. Head 20 serves as a handle means to facilitate handling of elongate sleeve 18.

The interior diameter of needle 12 is slightly greater than the exterior diameter of elongate sleeve 18 so that said elongate sleeve may be slideably received within said hollow needle 12. Hollow hub 16 is sized and configured to receive head 20 therewithin and thus serves as a stop means to limit the depth of insertion of said elongate sleeve 18 into hollow needle 12.

The interior diameter of sleeve 18 is slightly greater than the common exterior diameter of seeds 22 and spacers 24; said seeds and spacers are in axial alignment with one another to facilitate their introduction into the hollow interior of sleeve 18 as will be set forth hereinafter.

Stylet or push rod 26 is preferably of solid, i.e., nonhollow construction and has a flat leading end 28 for abutting against said seeds and spacers; it further includes a hub 30 it its trailing end that serves as a handle means. The external diameter of push rod 26 is slightly less than the internal diameter of sleeve 18 so that the former is slideably receivable within the latter. Sleeve 18 and push rod 26 share a substantially common extent with each other and with hollow needle 12.

Figure 2:
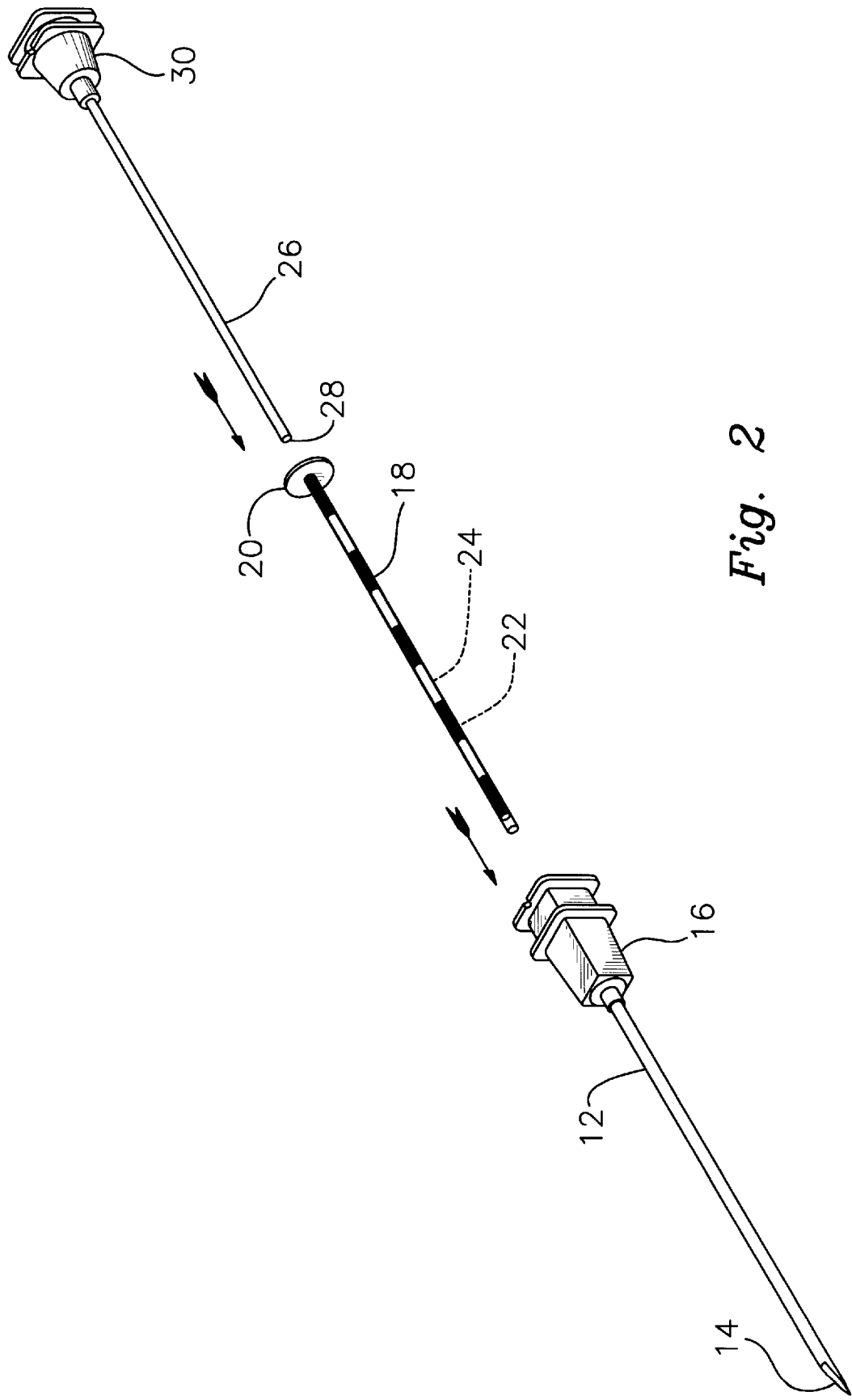
FIG. 2 is an exploded perspective view of the novel apparatus when the seeds and spacers are loaded within the novel sleeve member.

Significantly, elongate sleeve 18 is transparent or translucent. Accordingly, as depicted in FIG. 2, when seeds and spacers 22, 24 have been loaded into elongate sleeve 18, each seed and spacer remains visible therewithin. This enables the physician to determine whether or not elongate sleeve 18 has been properly loaded and to ascertain the number of seeds remaining within said elongate sleeve 18 at any time during the implanting procedure. In a preferred embodiment, elongate sleeve 18 is preloaded with seeds and spacers 22 and 24 at a remote facility so that the novel apparatus consists of the three parts depicted in FIG. 2 as far as the physician is concerned.

Figure 3:
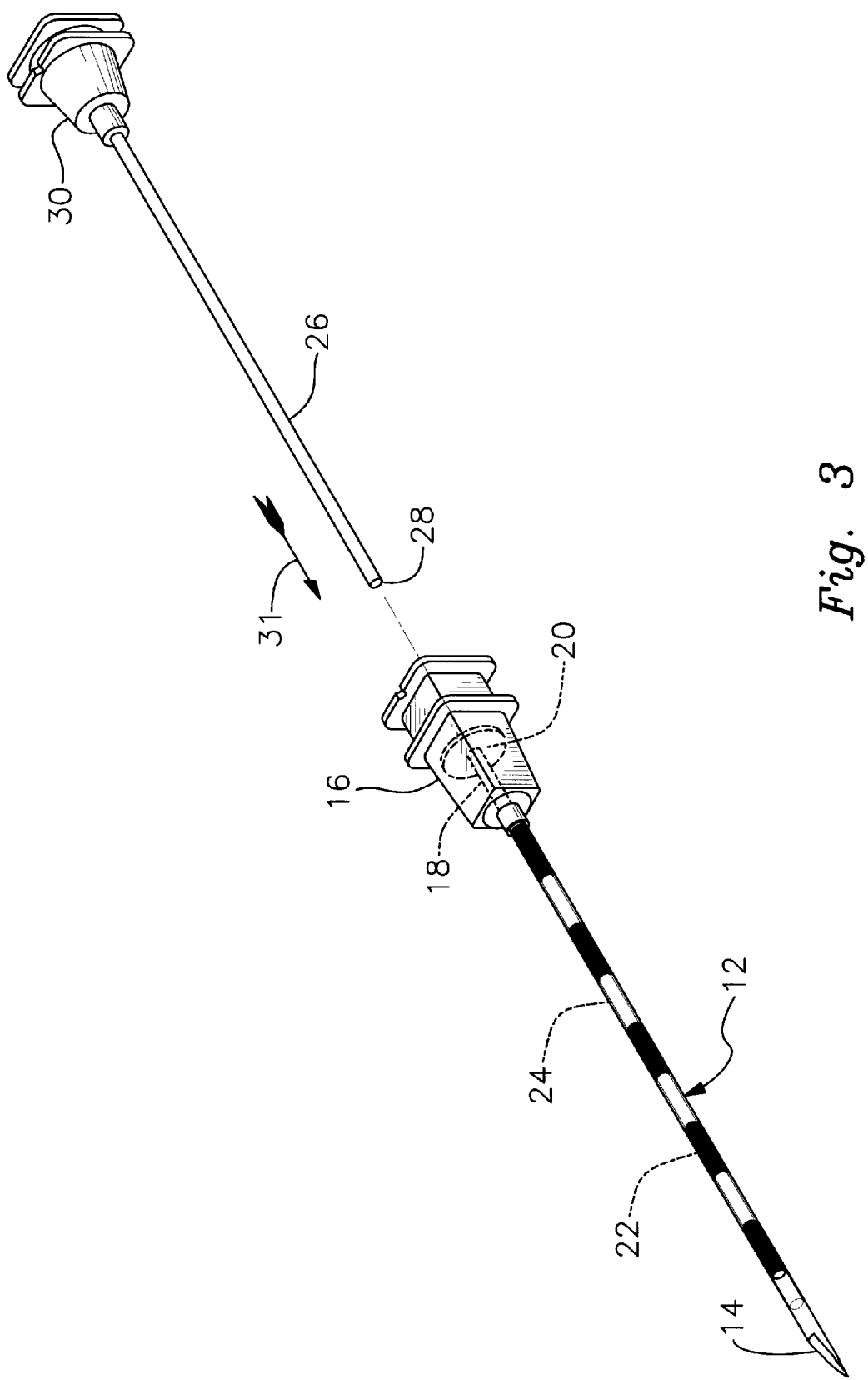
FIG. 3 is an exploded perspective view when the loaded sleeve member is received within the hollow needle.

To use novel apparatus 10, the physician first inserts loaded sleeve 18 into hollow needle 12; the resulting assembly is depicted in FIG. 3. Note how hub 16 of hollow needle 12 limits the depth of insertion of elongate sleeve 18 into hollow needle 12. Said hollow needle 12 is metallic and not transparent so the seeds and spacers cannot be seen in this configuration of the assembly. However, due to the sliding, loose fit of loaded sleeve 18 within hollow needle 12, the physician need merely tilt hub 16 downwardly relative to leading end 14, or lift leading end 14 upwardly relative to hub 16, to cause sleeve 18 to slide therefrom whenever it is desired to count the number of seeds and spacers remaining in loaded sleeve 18.

To implant a seed 22, the physician performs the usual preparatory steps and selects the first implantation site. Hollow needle 12 is inserted in a first direction (trailing-to-leading) into the prostate gland (or other tissue to be treated) to the desired depth, and push rod 26 is advanced in said first direction, indicated by arrow 31, so that leading end 28 thereof squarely abuts and bears against the trailing-most seed in elongate sleeve 18 so that all of the seeds and spacers in said elongate sleeve are prevented from traveling in a second direction opposite to that of arrow 31. If all of the seeds and spacers are to be implanted into the gland at that site, needle 12 and sleeve 18 are completely withdrawn, i.e., moved in said second direction (opposite the direction of arrow 31), over stationary push rod 26. If only one seed, or one seed and spacer are to be implanted at that site, needle 12 and sleeve 18 are retracted only the length of a seed, or the combined length of a seed and spacer, while the position of push rod 26 is maintained. Needle 12, sleeve 18, and push rod 26 are then collectively removed from the gland or other implantation site. The seed-implantation procedure is then repeated in accordance with the protocol for the patient.

Note that moving hollow hub 16 in said second direction carries elongate sleeve 18 in said direction as well because disc-shaped head 20 of said elongate sleeve is engaged by said hollow hub 16.

The provision of sleeve 18 and push rod 26 thus eliminates the need for vertically stacked seeds and spacers in a magazine and further eliminates the need for a bias means that urges such seeds sequentially into a magazine discharge chamber. The novel structure accordingly uses a minimal amount of materials and thus is inexpensive to manufacture. Just as importantly, it is easy to use. Moreover, it enables a physician to quickly determine at a glance the number of seeds and spacers remaining in the tool.

It will thus be seen that the objects set forth above, and those made apparent from the foregoing description, are efficiently attained and since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A tool for implanting radioactive seeds in tissue, comprising:

an elongate hollow needle having a pointed leading end for facilitating introduction of said hollow needle into tissue at a preselected site;

a hollow elongate sleeve having an external diameter slightly less than an internal diameter of said hollow needle;

a plurality of radioactive seeds and nonradioactive spacers adapted to be slideably received within a hollow interior of said elongate sleeve, said seeds and spacers having a common external diameter slightly less than an internal diameter of said elongate sleeve; and an elongate push rod having a longitudinal extent substantially equal to a longitudinal extent of said elongate sleeve;

wherein said hollow needle slideably receives said elongate sleeve when said seeds and spacers are loaded into said elongate sleeve; and whereby said seeds and spacers are displaced from said elongate sleeve and hence from said hollow needle by retracting said hollow needle and elongate sleeve while maintaining said push rod in a fixed position.

2. The tool of claim 1, wherein said elongate sleeve has a longitudinal extent substantially equal to a longitudinal extent of said hollow needle.

3. The tool of claim 1, wherein said push rod has a longitudinal extent substantially equal to a longitudinal extent of said hollow needle.

4. The tool of claim 1, wherein said elongate sleeve is transparent so that a physician may visually determine the number of seeds and spacers remaining in said elongate sleeve at any time it is not in said needle.

5. The tool of claim 1, wherein said elongate sleeve is translucent so that a physician may visually determine the number of seeds and spacers remaining in said elongate sleeve at any time it is not in said needle.

6. The tool of claim 1, further comprising a handle mounted to said elongate sleeve at a trailing end of said elongate sleeve to facilitate handling of said elongate sleeve.

7. The tool of claim 6, further comprising a hollow hub mounted at a trailing end of said hollow needle, said hollow hub having a size and configuration adapted to receive therewithin said handle of said elongate sleeve when said elongate sleeve is slideably received within said hollow needle, said hollow hub limiting a depth-of insertion of said elongate sleeve into said hollow needle, said hollow hub further providing a handle means that facilitates handling of said hollow needle, and said hollow hub engaging a head of said elongate sleeve when said hollow needle is retracted from said tissue.

8. The tool of claim 1, further comprising a handle means formed at a trailing end of said push rod to facilitate handling of said push rod.

9. The tool of claim 8, wherein said push rod has a flat leading end to facilitate pushing of said seeds and spacers from said elongate sleeve.

10. A method of implanting radioactive seeds into tissue, comprising the steps of:

providing an elongate hollow needle having a pointed leading end to facilitate its introduction into said tissue and having a hollow hub at its trailing end;

providing a hollow elongate sleeve having a head member at its trailing end and sized so that it has an extent substantially equal to an extent of said hollow needle and so that said elongate sleeve is slideably receivable within said hollow needle;

providing an elongate push rod having an extent substantially equal to that of said hollow needle and said elongate sleeve and sized so that it is slideably receivable within said elongate sleeve;

wherein said hollow hub of said hollow needle and said head member of said elongate sleeve are sized and configured so that said hollow hub receives said head member therewithin when said elongate sleeve is slideably received within said hollow needle;

loading a plurality of axially aligned radioactive seeds into said elongate sleeve;

loading said elongate sleeve into said hollow needle;

introducing said hollow needle into said tissue at a preselected site and at a predetermined depth by advancing said needle in a first direction;

inserting a leading end of said push rod into a trailing end of said elongate sleeve so that said leading end of said push rod bears against a seed positioned within said elongate sleeve and prevents movement of said seed in a second direction opposite to said first direction; and maintaining said push rod in abutting relation to said seed while simultaneously retracting said hollow needle and said elongate sleeve in said second direction a predetermined distance so that at least one seed is left implanted in said tissue, said hollow hub of said hollow needle engaging said head member of said elongate sleeve and carrying said elongate sleeve in said second direction.

* * * * *